(12) United States Patent
Harper

(10) Patent No.: US 7,128,258 B1
(45) Date of Patent: Oct. 31, 2006

(54) OPTICAL IMMUNIZATION CARD

(75) Inventor: W. Jack Harper, Evergreen, CO (US)

(73) Assignee: BSI2000, Inc., Lakewood, CO (US)

( * ) Notice: Subject to any disclaimer, the term of this patent is extended or adjusted under 35 U.S.C. 154(b) by 0 days.

(21) Appl. No.: 11/056,177

(22) Filed: Feb. 10, 2005

Related U.S. Application Data

(60) Provisional application No. 60/543,617, filed on Feb. 10, 2004.

(51) Int. Cl.
G06F 17/00 (2006.01)

(52) U.S. Cl. ..................................... 235/375
(58) Field of Classification Search ................. 235/375
See application file for complete search history.

(56) References Cited

U.S. PATENT DOCUMENTS

| | | |
|---|---|---|
| 4,396,914 A | 8/1983 | Aston |
| 4,500,777 A | 2/1985 | Drexler |
| 4,542,288 A | 9/1985 | Drexler |
| 4,544,835 A | 10/1985 | Drexler |
| 4,572,891 A | 2/1986 | Drexler |
| 4,598,196 A | 7/1986 | Pierce et al. |
| 4,665,004 A | 5/1987 | Drexler |
| 4,683,371 A | 7/1987 | Drexler |
| 4,901,241 A | 2/1990 | Schneck |
| 4,917,292 A | 4/1990 | Drexler |
| 5,214,699 A | 5/1993 | Monroe et al. |
| 5,268,963 A | 12/1993 | Monroe et al. |
| 5,412,727 A | 5/1995 | Drexler et al. |
| 5,421,619 A | 6/1995 | Dyball |
| 5,457,747 A | 10/1995 | Drexler et al. |
| 5,559,885 A | 9/1996 | Drexler et al. |
| 5,865,470 A * | 2/1999 | Thompson .................... 283/70 |
| 5,932,865 A | 8/1999 | Drexler |
| 5,960,403 A | 9/1999 | Brown |
| 5,992,891 A | 11/1999 | Dyball |
| 6,022,315 A | 2/2000 | Iliff |
| 6,199,761 B1 | 3/2001 | Drexler |
| 6,266,647 B1 | 7/2001 | Fernandez |
| 6,290,130 B1 | 9/2001 | Drexler |
| 6,318,633 B1 | 11/2001 | Drexler |
| 6,338,433 B1 | 1/2002 | Drexler |
| 6,473,861 B1 | 10/2002 | Stokes |
| 2002/0100803 A1* | 8/2002 | Sehr ........................... 235/384 |
| 2003/0204417 A1* | 10/2003 | Mize ............................ 705/2 |
| 2004/0124246 A1* | 7/2004 | Allen et al. ................. 235/492 |
| 2004/0138535 A1* | 7/2004 | Ogilvie ........................ 600/300 |
| 2004/0255081 A1* | 12/2004 | Arnouse ..................... 711/115 |

FOREIGN PATENT DOCUMENTS

DE 313428 7/1919

* cited by examiner

*Primary Examiner*—Jared J. Fureman
*Assistant Examiner*—Tae W. Kim
(74) *Attorney, Agent, or Firm*—Townsend and Townsend and Crew LLP; William F. Vobach

(57) ABSTRACT

A system is provided for providing security with an optical card. According to one embodiment of the invention, immunization data can be disposed on an optical card and used in an optical card system to establish that a particular individual has been immunized for a particular disease. The immunization data can be stored in a variety of formats and encrypted for verification. Biometric data can be used with the immunization data to establish that the immunization data applies to that particular individual. The optical card memory allows sufficient biometric data to be stored so as to clearly verify the identity of the card holder.

3 Claims, 13 Drawing Sheets

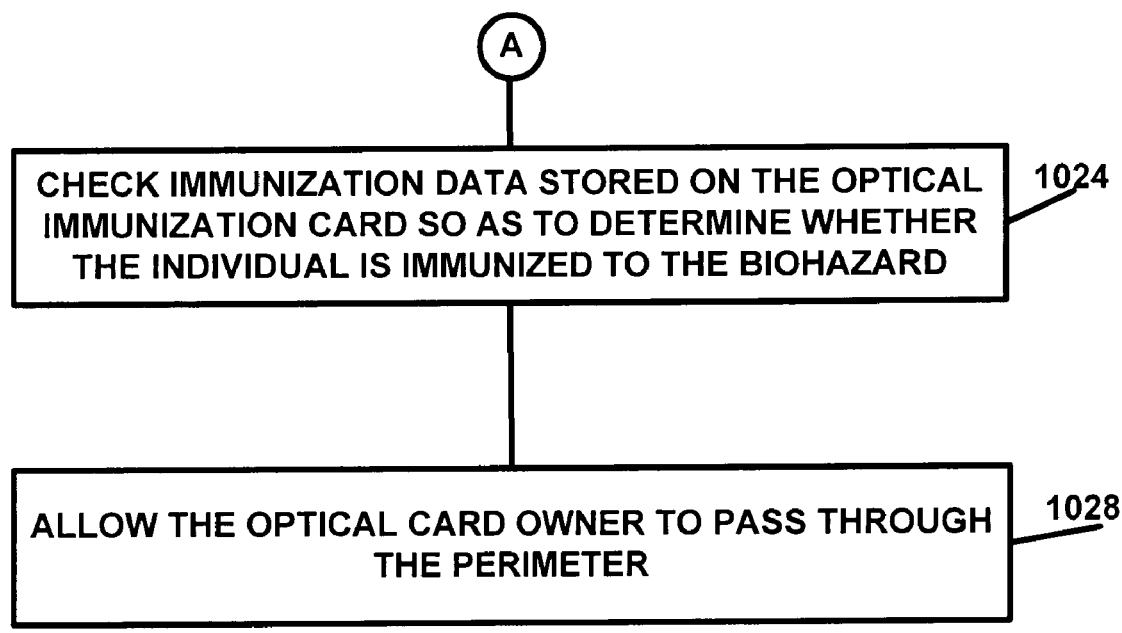
FIG.
10B

OPTICAL IMMUNIZATION CARD

CROSS-REFERENCES TO RELATED APPLICATIONS

This application claims the benefit of U.S. Provisional Application 60/543,617, filed Feb. 10, 2004, entitled "Optical Card Security System", which is hereby incorporated by reference for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

The present embodiments of the invention relate generally to optical cards. More particularly, one embodiment of the invention relates to use of an optical card to enforce security at a biohazardous site.

BACKGROUND

With the advent of terrorist attacks on the United States, it is ever more apparent that there is a need for increased security in our everyday lives. One such threatened attack is through the use of biohazardous material which often can take the form of bio-engineered or existing contagious diseases. An example of one such dangerous disease is smallpox. While smallpox has essentially been eradicated in North America and well-developed areas of the world, it still poses a threat to those who have not been immunized from it. Similarly, other diseases, such as the Ebola virus, are extremely contagious and dangerous to large populations as well.

In the past year, the illness known as Severe Acute Respiratory Syndrome (SARS) has made apparent the vulnerability of large populations to a contagious disease. Furthermore, this illness has demonstrated that people in afflicted areas will flee the infected area to escape the disease without knowing whether they are a carrier of the disease. It was observed that people in quarantined areas would attempt to flee those areas without regard to the effect that their condition would have on others that they came into contact with outside the quarantined area. Therefore, this has clearly demonstrated that people are willing to break the law or lie so as to escape a biohazardous site.

Similarly, there are those people who will put their own health at risk to enter a biohazardous site—either to retrieve possessions or contact loved ones. It is common to see people cross police barricades when trying to return to homes that have been evacuated for natural disasters such as forest fires and hurricanes. Undoubtedly, the same mentality would prevail for some people if a biohazardous situation were to develop, preventing people from returning to their homes or loved ones.

Therefore, there is a need for a system which can be used to help establish that an individual is immunized to a particular threat. Furthermore, a verification system is desired that will help prevent an individual from forging his or her immunization to a particular threat. Similarly, there is a need for a system to establish that someone has been immunized to a particular threat so as to allow them to enter or exit to a currently quarantined area.

BRIEF SUMMARY

One embodiment of the invention provides an immunization system using an optical immunization card which comprises an optical card comprising a storage area for storing information accessible via an optical card reader; a first area of the optical card storing a set of data which is representative of a picture of the optical card owner; a second area of the optical card storing a first biometric set of data which is representative to an optical card reader of a first biometric of the optical card owner; and a third area of the optical card storing an immunization record for the optical card owner wherein the immunization record is readable by the optical card reader after the optical card reader utilizes the first biometric set of data.

Another embodiment of the invention provides an optical immunization card comprising an optical card comprising a storage area for storing information accessible via an optical card reader; a first area of the optical card storing a first biometric set of data representative to an optical card reader of a first biometric of the optical card owner; a second area of the optical card storing a second biometric set of data representative to an optical card reader of a second biometric of the optical card owner wherein the second biometric comprises a fingerprint of the optical card owner; a third area of the optical card storing a third biometric set of data representative to an optical card reader of a third biometric of the optical card owner wherein the third biometric is a signature of the optical card owner; and a fourth area of the optical card storing an immunization record for the owner, wherein the immunization record is readable by the optical card reader after the optical card reader utilizes the first biometric set of data by obtaining identification data for an individual; obtaining an optical card comprising a storage area for storing information accessible via an optical card reader; combining the identification data and the immunization data as a composite set of data; and storing the combined set of data on the optical card.

Another embodiment of the invention provides a method of securing ingress or egress to a biohazard contaminated scene by establishing a perimeter around the biohazard contaminated scene so as to restrict egress from the scene; establishing at least one exit area along the perimeter so as to allow immunized individuals to exit from the biohazard contaminated scene; providing an optical card reader operable for reading optical immunization cards; reading at least one optical immunization card provided by an individual; verifying the ownership of the optical immunization card by utilizing the optical immunization card; checking immunization data stored on the optical immunization card so as to determine whether the individual is immunized to the biohazard; and allowing the optical card owner to pass through the perimeter.

Further embodiments of the invention will be apparent to those of ordinary skill in the art from a consideration of the following description taken in conjunction with the accompanying drawings.

BRIEF DESCRIPTION OF THE DRAWINGS

FIGS. 10A and 10B are a flowchart illustrating a method of securing a biohazardous site with an optical immunization card, according to one embodiment of the invention.

DETAILED DESCRIPTION

Figure 1:
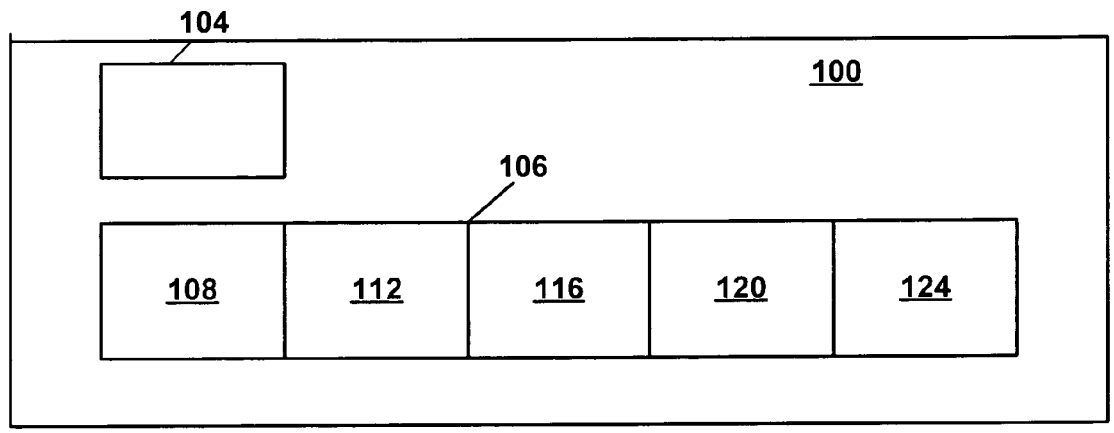
FIG. 1 is an optical immunization card, according to one embodiment of the invention.

In the world of security, biometric data is often used as a way to authenticate a specific person to be who they say they are. In an electronic world, this can be accomplished by comparing biometric data against a database of stored biometric data for that particular individual. However, in the physical world where one often does not have access to databases or does not trust databases of information, it is quite impossible to authenticate an individual's biometric data. One way to solve this is through the use of an optical card to carry the biometric data.

Optical cards are capable of storing a tremendous amount of data. For example, a typical optical card can store up to four megabytes—about 1500 pages of typewritten information—of updatable digital data in a secure, inexpensive and compact personal package. Optical cards hold on the order of 1,000 times the amount of information as the typical smart card and the data, once written, is permanent and cannot be erased or altered. Furthermore, optical cards, unlike smart cards, are impervious to electric and magnetic fields and also to static electricity. They are not damaged by bending or flexing and have a ten-year life with normal use. The large amount of reliable and permanent memory ensures that optical cards can easily hold information, such as high resolution digital photos of the card holder, multiple biometrics, such as all ten fingerprints, both of the individual's irises, hand geometries, signature biometrics, and many other biometrics. For example, fingerprint biometrics for all ten fingers, iris biometrics for both eyes, and a high resolution color photograph of the card holder would use far less than 1% of the capacity of an optical card.

Thus, optical cards are ideally suited to store a significant amount of biometric data that can be used on a transportable basis to authenticate an individual to someone who does not know that individual or does not know specific information about that individual, such as the immunization status of the individual. Furthermore, in addition to the large data storage made available by optical cards, the physical durability of optical cards is a great advantage in the security world. It is known to be able to render electronic devices useless through the use of electromagnetic pulses that essentially destroy the operability of the circuits of these electronic devices. Thus smart cards are subject to such an attack. Similarly, smart cards, for example, have limited physical flexibility compared to very thin optical cards, which can be carried in an individual's wallet with little fear of rendering the card inoperable due to bending. Quite simply, optical cards are extremely durable and flexible without fear of destroying data stored on the card. Moreover, they are permanent in that electromagnetic fields have no effect on their storage of data. Namely, they are a physical medium which are "write once/read many times." Thus, optical cards are a useful medium for storing the data which is required in many security settings.

Referring now to FIG. 1, an exemplary optical card can be seen. Optical card 100 is shown in this example as having a photograph area 104 for storing the individual photo of the optical card owner. While optical cards might be issued by government agencies or private organizations, for purposes of this patent, it should be understood that the phrase "the optical card owner" refers to the person who uses the optical card. For example, if the optical card is used as an identification card, then the owner in that case would be the person identified by the optical card. It is not intended, in such a situation, to refer to the person who manufactured or issued the card, such as the government organization.

Referring again to FIG. 1, exemplary optical card 100 has a memory storage area 106. This memory storage area is shown comprised of individual sections 108, 112, 116, 120 and 124. Each of these sections can be accessed to store or retrieve information. Furthermore, each section can be designated by an addressing system to refer to formatted data stored or designated for each individual section. It will be apparent to one of ordinary skill in the art how to address the individual sections and retrieve information from those sections. Many optical memory cards use a technology similar to the one used for music CDs or CD ROMs. For example, a panel of gold colored laser sensitive material can be laminated in the card and used to store the information. The material can be comprised of several layers that react when a laser light is directed at them. The laser burns a tiny hole (2.25 microns in diameter) in the material which can then be sensed by a low power laser during the read cycle. The presence or absence of the burn sport indicates a "one" or a "zero". Because this material is actually burned during the write cycle, the media is write once read many (WORM) media and the data is non volatile (not lost when power is removed). These optical cards can currently store between 2 and 4 MB of data which give them the ability to store graphical images such as photographs, logos, fingerprints, x-rays, etc. The data can be encoded in a linear x-y format and ISO/IEC 11693 and 11694 standards cover the details, the contents of which are hereby incorporated by reference for all purposes.

Referring again to FIG. 1, section 108 can be used to store a first biometric set of data representing a first biometric of the user. For example, section 108 can store the digitized signature of an individual. Similarly, section 112 can store the digitized photograph of an individual. Section 116 could store all ten fingerprints of the individual. Other biometric sets of data could be stored on other areas of the card.

Figure 2:
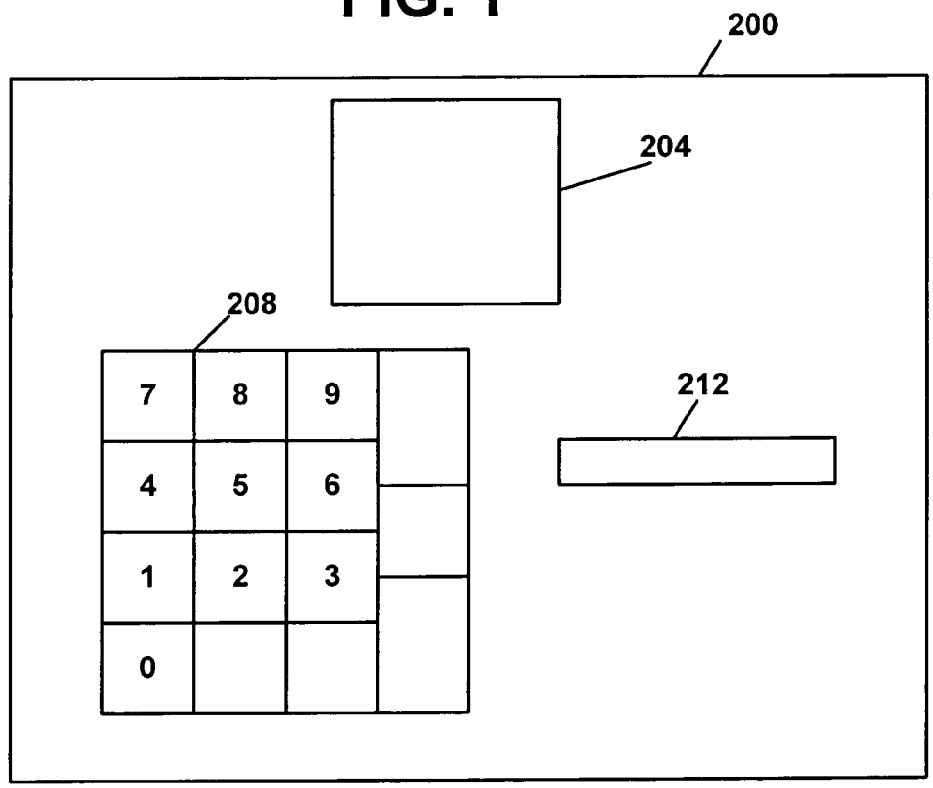
FIG. 2 is an optical card reader, according to one embodiment of the invention.

Referring now to FIG. 2, an optical card reader is shown. This reader could be a permanent reader used in an office and coupled to a computing system. Alternatively, it could be a portable or mobile system with a transmitter that could transmit to a computing system. While a separate computing system is not required for an optical card reader, it is envisioned that in many instances one will want to communicate the data to a computer system for storage. FIG. 2 shows the optical card reader 200 as having a screen 204 for displaying instructions to the user and biometric data retrieved from an optical card for comparison to the individual's real-time presentation of the biometric data. For example, the screen could be used to display a digitized photograph of the optical card owner or the handwritten signature of the optical card owner. Depending on the computing power of the optical card reader, there are functions to be implemented through software to manipulate the stored biometric data and the retrieved biometric data. For example, a stored biometric signature could be compared to a real-time signature of the optical card owner at a digital tablet coupled with the applicable card reader. Furthermore, FIG. 2 shows a keyboard 208 for entering information. A numeric pad is shown in this example, but a full keyboard could be used as well. Finally, FIG. 2 shows a slot 212 for inserting an optical card for reading by the optical card reader. Thus, the optical card reader can retrieve stored information from the optical card in the secured environment of the reader.

Figure 3:
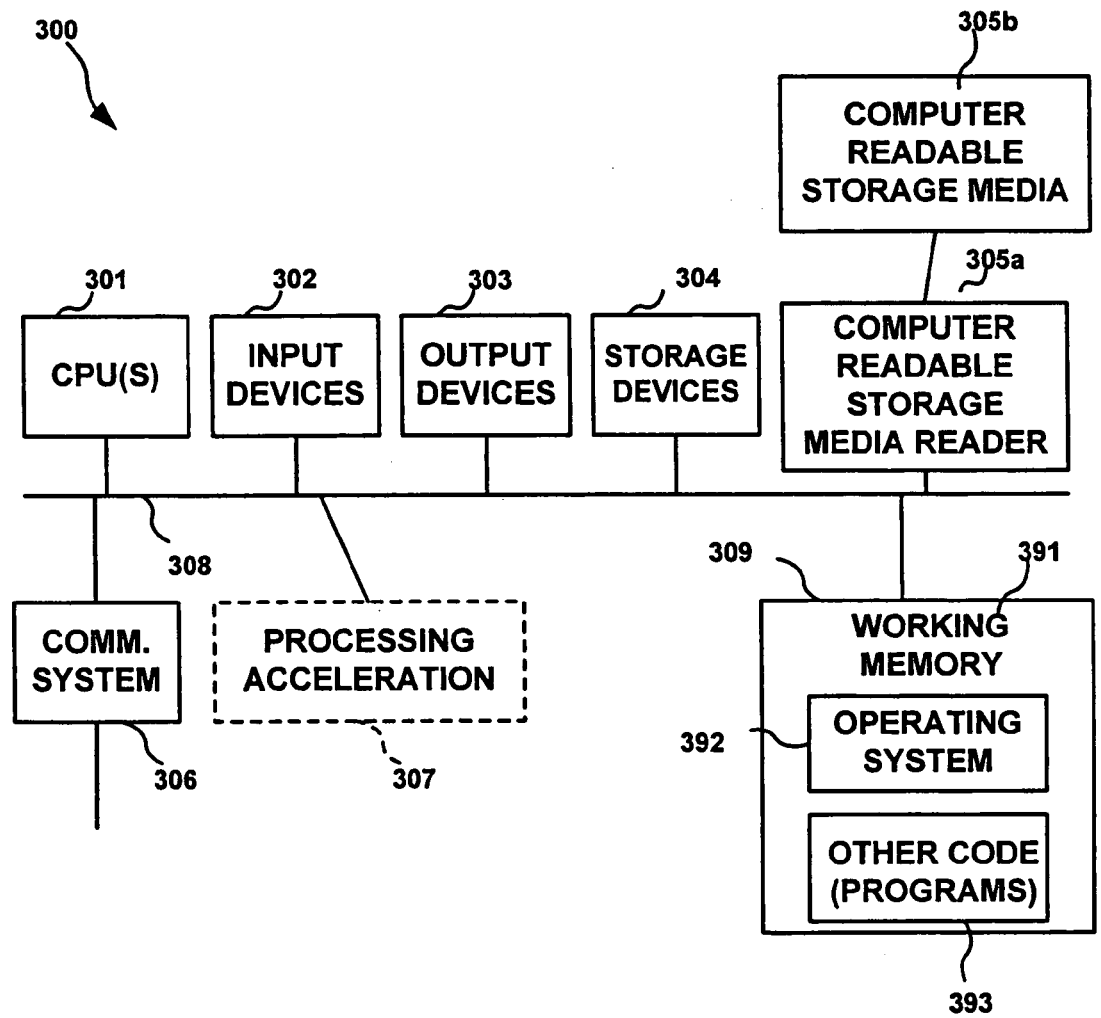
FIG. 3 is an exemplary computer system used, for example, in the optical card reader of FIG. 2.

Referring now to FIG. 3, a computing system 300 for implementing optical card reader 200 is shown. This is merely an example of one computing system that could be used to implement the optical card reader. System 300 is shown comprised of hardware elements that are electrically coupled via bus 308, including a processor 301, input device 302, output device 303, storage device 304, computer-readable storage media reader 305a, communications system 306 processing acceleration (e.g., DSP or special-purpose processors) 307 and memory 309. Computer-readable storage media reader 305a is further coupled to computer-readable storage media 305b, the combination comprehensively representing remote, local, fixed and/or removable storage devices plus storage media, memory, etc. for temporarily and/or more permanently containing computer-readable information, which can include storage device 304, memory 309 and/or any other such accessible system 300 resource. System 300 also comprises software elements (shown as being currently located within working memory 391) including an operating system 392 and other code 393, such as programs, applets, data and the like.

Figure 4A:
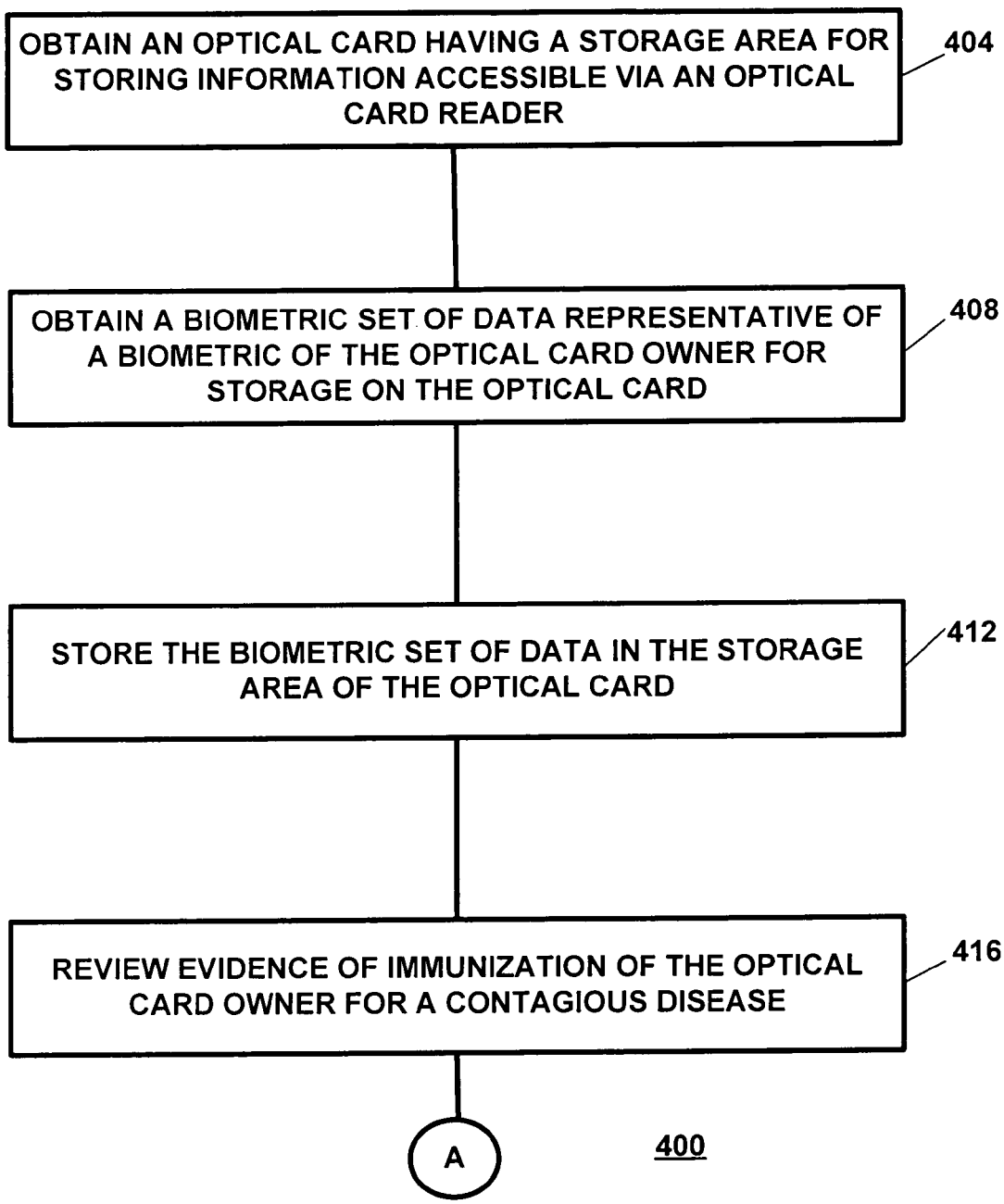
FIGS. 4A and 4B are a flowchart illustrating a method of configuring an optical immunization card, according to one embodiment of the invention.
Figure 4B:
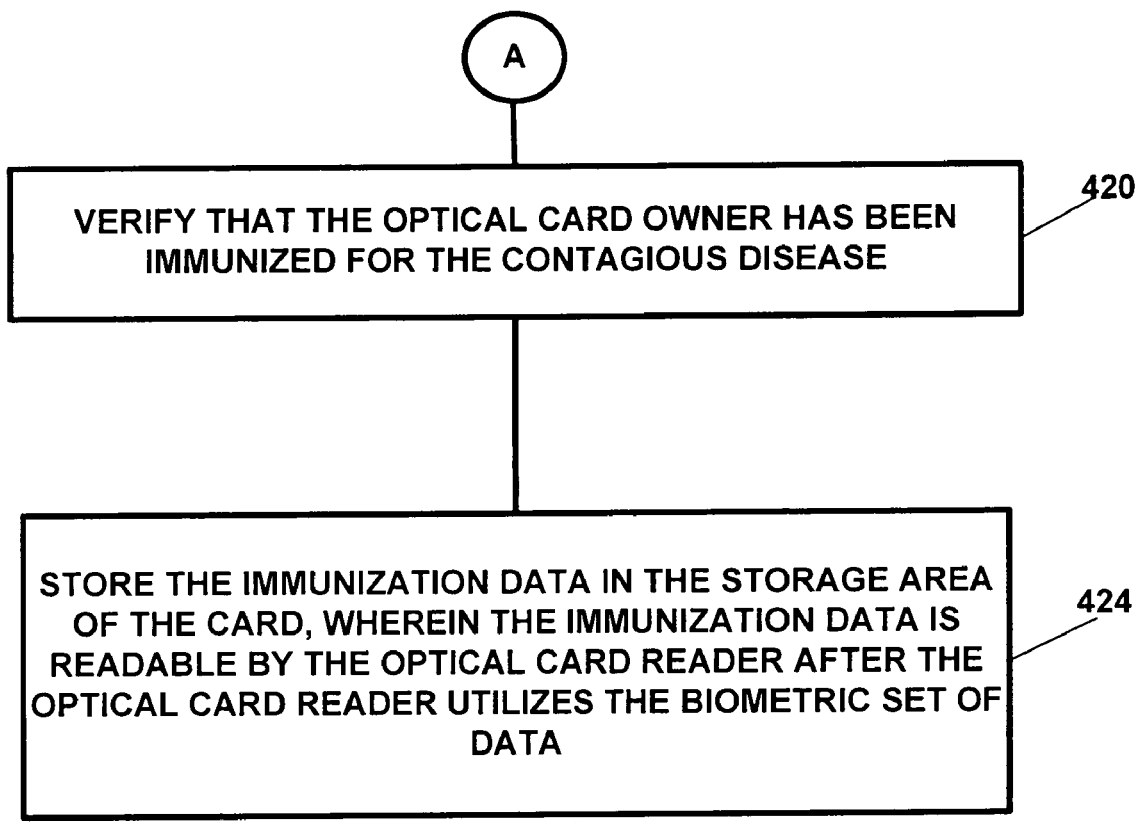

Referring now to FIGS. 4A and 4B, a flowchart 400 shows a method for implementing one embodiment of the invention. In block 404, an optical card is obtained having a storage area for storing information accessible via an optical card reader. In block 408, a biometric set of data is obtained wherein the biometric set of data is representative of a biometric of the optical card owner for storage on the optical card. One example of a biometric set of data is a digitized signature of the optical card owner. In block 412, the biometric set of data is stored in the storage area of the optical card. Referring to FIG. 1, storage area 106 can be used to store the biometric set of data. In block 416, evidence is reviewed of the immunization of the optical card owner for a contagious disease. Such evidence might be a card presented by the optical card owner from a physician's office. Similarly, one might even issue the optical card at a doctor's office to ensure that the evidence truly does evidence the immunization of the optical card owner. Thus, it is envisioned that optical cards could be updated or issued at physician's offices throughout the country through the use of an optical card reader and an optical card owned by the patient. In block 420, a verification is performed to ensure that the optical card owner has been immunized for the contagious disease. Thus, for example, the evidence obtained in block 416 is reviewed and verified to ensure its credibility and ensure that no forgery has taken place. In block 424, the immunization data is stored in the storage area of the optical card, wherein the immunization data is readable by the optical card reader after the optical card reader utilizes the biometric set of data. This will be explained in greater detail below.

Figure 5A:
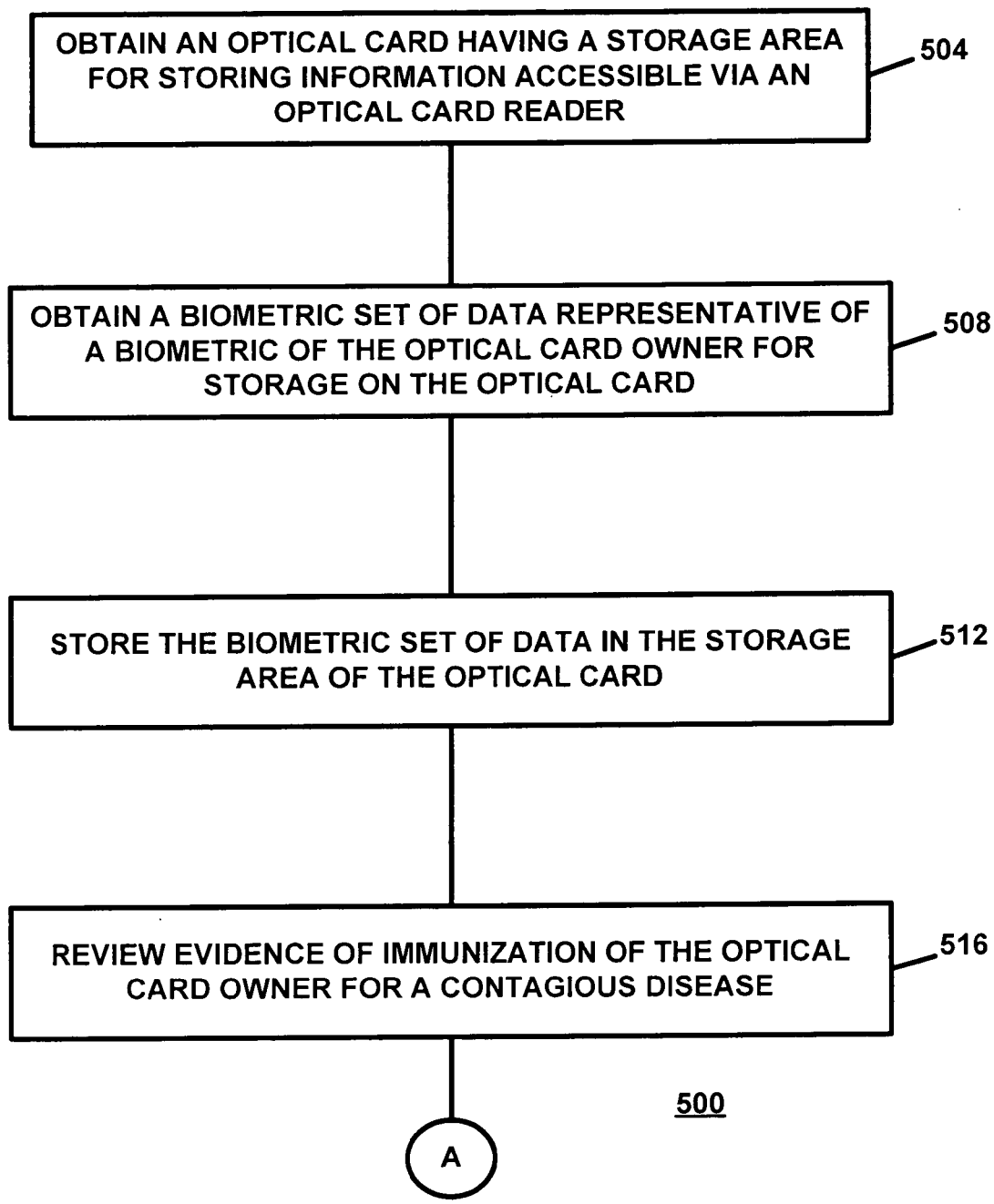
FIGS. 5A and 5B are a flowchart illustrating a method of configuring an optical immunization card, according to one embodiment of the invention.
Figure 5B:
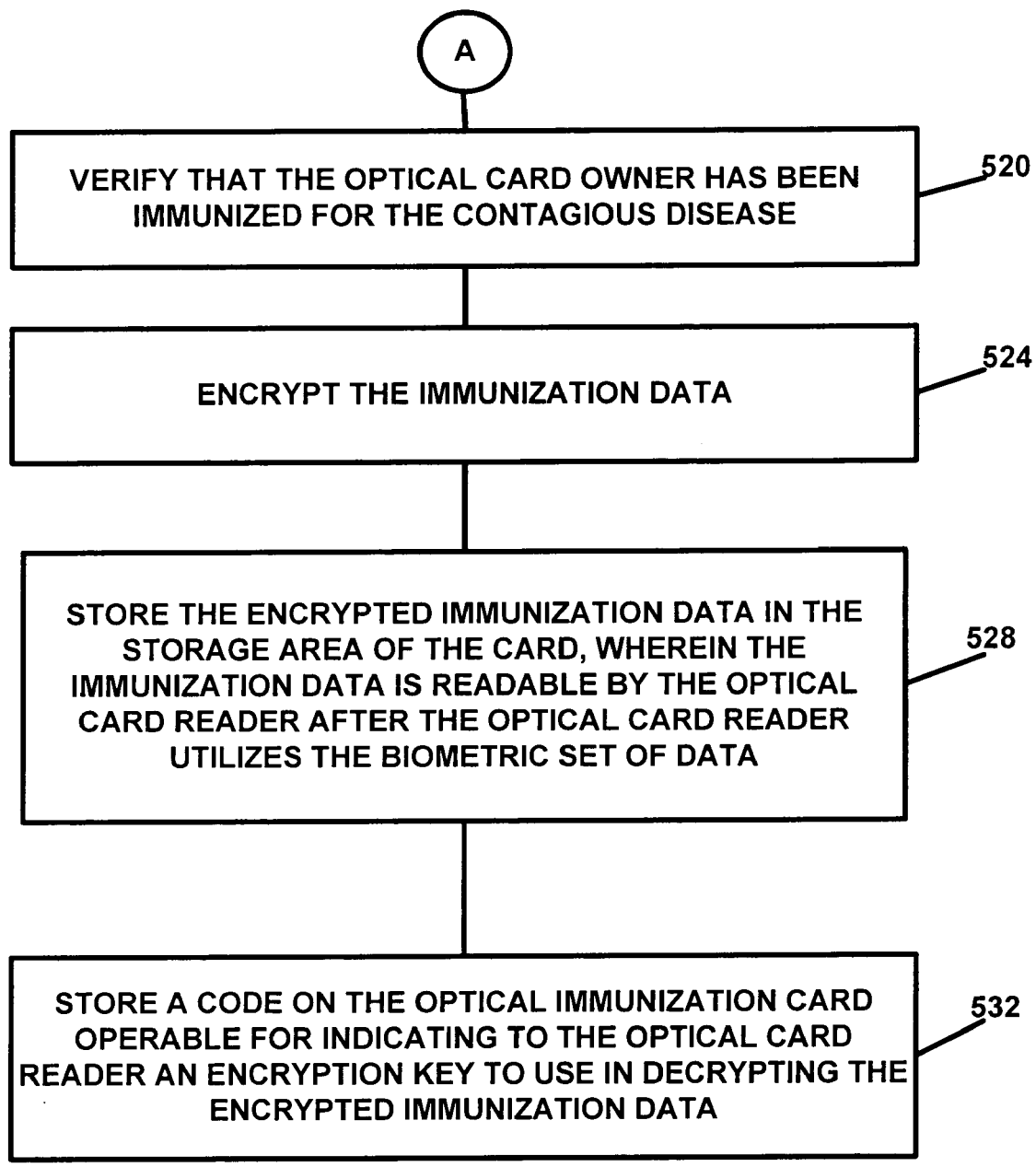

FIGS. 5A and 5B show a flowchart 500 which illustrates a more detailed embodiment of the invention. Namely, in block 504 of flowchart 500, an optical card is obtained having a storage area for storing information accessible via an optical card reader. Again, FIG. 1 shows a storage area 106 having individual portions 108, 112, 116, 120, and 124, which are accessible via an optical card reader. The optical card reader can both read from and write to the storage area on optical card 100. In block 508, a biometric set of data representative of a biometric of the optical card owner is obtained for storage on the optical card. For example, such biometrics can include a signature of the optical card owner, a high resolution photograph of the optical card owner such as a profile and a head-on view, a digitized set of data for the irises of an optical card owner, a set of digitized fingerprints for each finger of the optical card owner, a voice print of the optical card owner, a digitized DNA sampling of the optical card owner, or other biometric data that is helpful in identifying an individual. In block 512, the biometric set of data is stored in the storage area of the optical card. The biometric data can be stored in a particular area depending on the formatting of the optical card. It is envisioned that a standardized system will be used to store various information in particular storage areas of the optical card. Thus, the storage area can be divided to store a photograph in a predesignated area of the memory, a signature in another predesignated area of the card, and fingerprint data in yet another predesignated storage area of the card. In block 516, evidence is reviewed of the immunization of the optical card owner for a contagious disease. For example, an immunization certificate from a physician can be reviewed to confirm that a particular individual has been immunized for smallpox. In block 520, the immunization evidence reviewed in block 516 is verified so as to authenticate that the immunization for the contagious disease actually took place. Thus, as explained above, the verification may simply be accomplished by checking an immunization card of the individual or by an authority actually watching the administration of the immunization to a particular individual. The verification can vary, depending upon the agency making the representation that a particular individual has been immunized. In block 524, the immunization data in this particular example is encrypted prior to storage on the optical immunization card. In block 528, the encrypted immunization data is stored in the storage area of the card, wherein the immunization data is readable by the optical card reader after the optical card reader utilizes the biometric set of data.

According to one embodiment, the optical card reader will first obtain the biometric data on the optical card prior to utilizing the immunization data. This is so that the optical card reader can ensure that the individual presenting the immunization data is actually the person for whom the immunization data was stored. Thus, the optical card reader uses an authentication protocol to first ensure that the person presenting the immunization data is the person for whom the immunization data was generated. Once the optical card reader can authenticate the individual, the immunization data can be retrieved. As part of the process for retrieving the immunization data after verifying the biometric data, one might utilize a protocol that retrieves a decryption key after reviewing the biometric data. Furthermore, the encryption key might be a particular designated area within the biometric data itself. For example, it could be a string of characters within a biometric associated with the immunization data. Alternatively, the decryption might merely be stored on the optical card reader itself. Furthermore, it could be accessible via a database once the optical card is read. With the decryption key, the immunization data can then be decrypted to retrieve the human-readable data presented at the optical card reader. Thus, the immunization details for smallpox, for example, can be retrieved and decrypted before being displayed on the optical card reader for security personnel to review. In block 532, a code is stored on the optical immunization card that is operable for indicating to the optical card reader an encryption key to use in decrypting the encrypted immunization data. As explained earlier, this code could be disposed in a portion of the biometric data or alternatively it could be disposed on another location of the optical card. In one embodiment, it might merely be disposed as part of the encrypted immunization data itself.

Figure 6A:
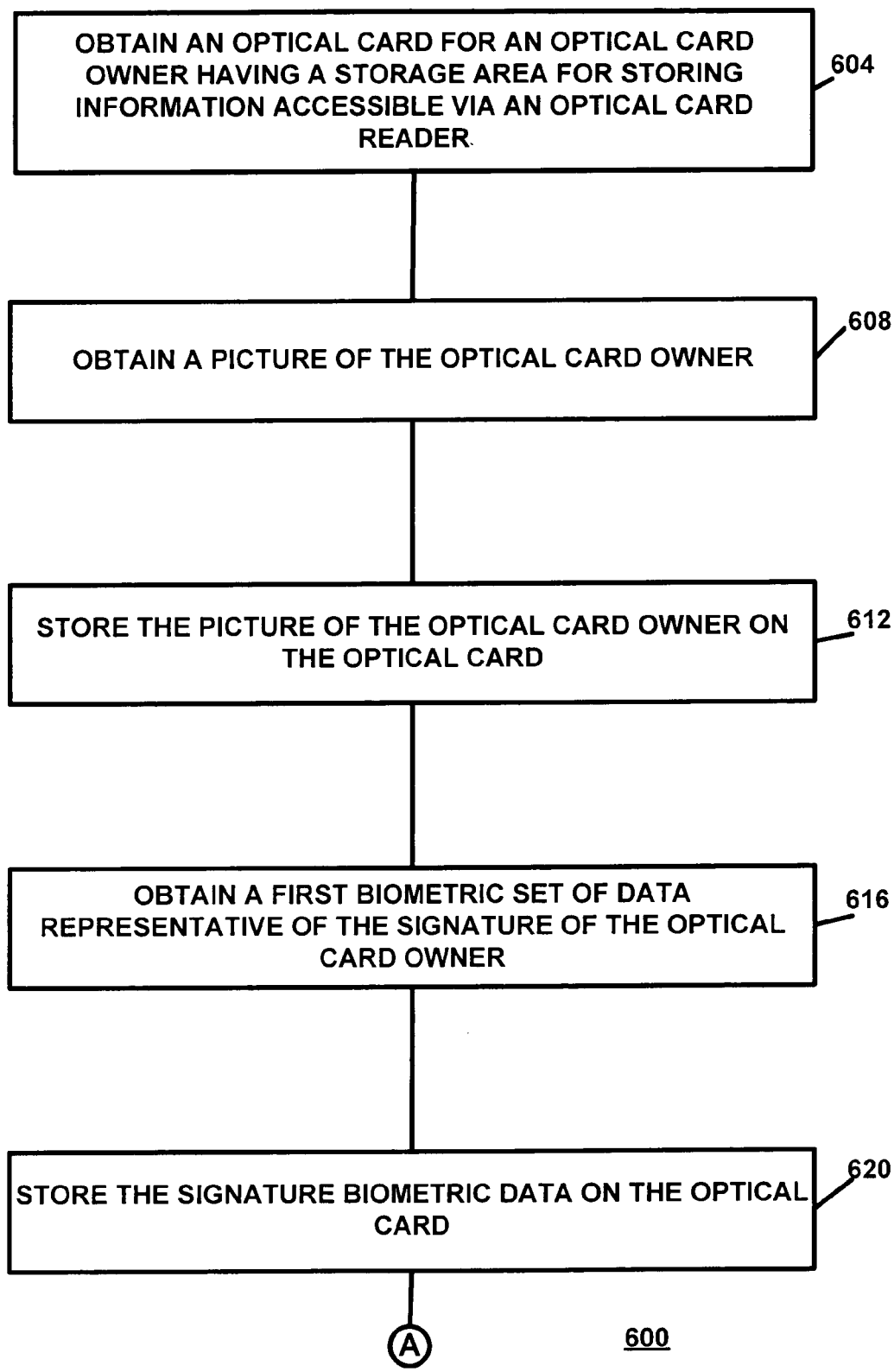
FIGS. 6A and 6B are a flowchart illustrating a method of configuring an optical immunization card, according to one embodiment of the invention.
Figure 6B:
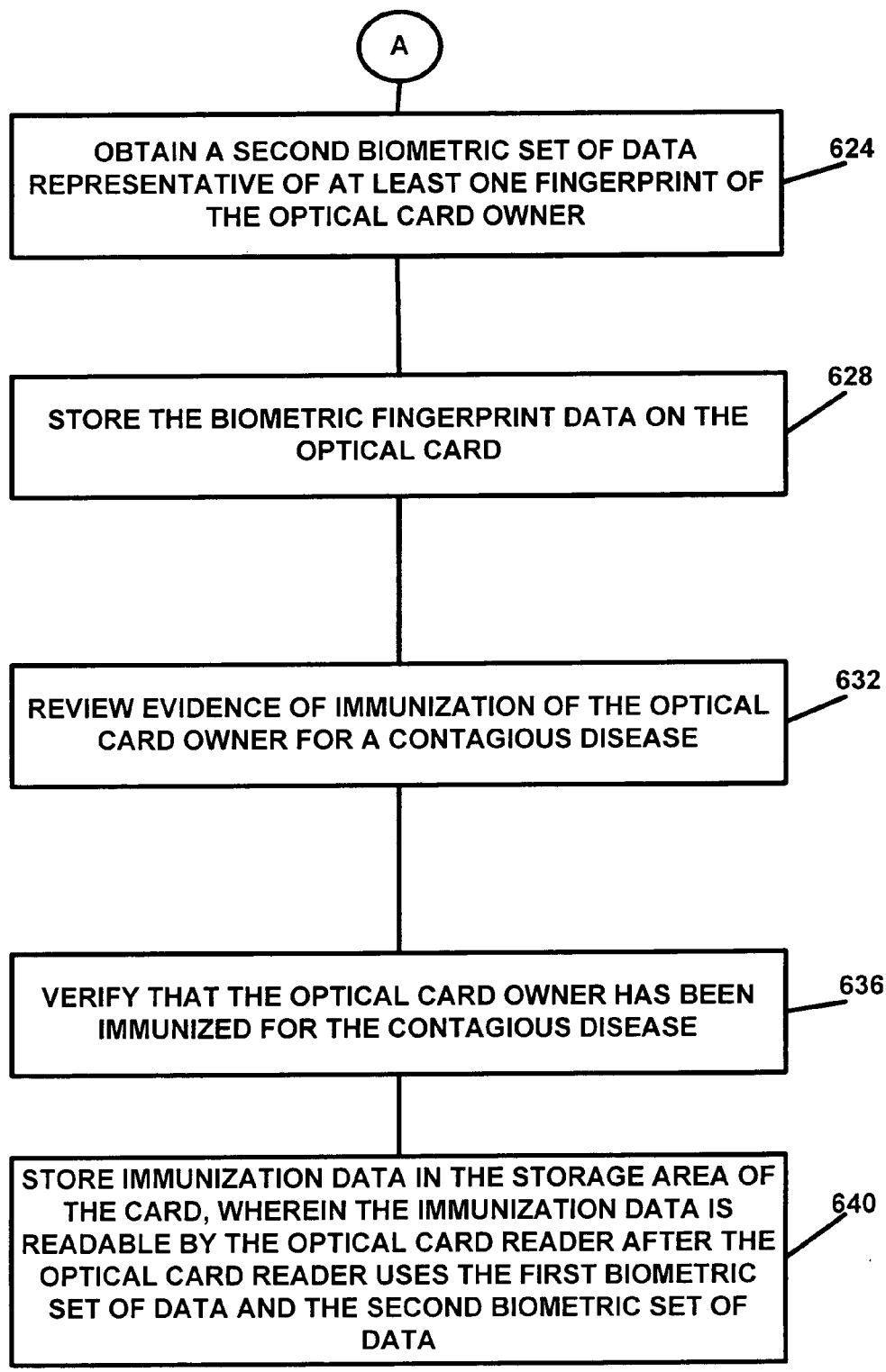

FIGS. 6A and 6B illustrate yet another embodiment of the invention. The flowchart 600 shown in FIGS. 6A and 6B illustrates a biometric intensive embodiment of the invention. Namely, multiple use is made of the various biometrics stored on an optical immunization card for purposes of determining the immunization status of an individual. In block 604, an optical card is obtained for an optical card owner having a storage area for storing information accessible via an optical card reader. In block 608, a picture of the optical card owner is obtained. In block 612, the picture is stored on the optical card It should be understood that a picture of an optical card owner could be used as either a physical picture disposed on a card so as to be viewable by someone looking at the card itself or stored as a set of biometric data in one of the storage areas of the card. In some instances, one may desire to configure the card with both a physical picture and a digital set of data representing the picture, rather than just one or the other. In block 616, a biometric set of data is obtained that is representative of the signature of the optical card owner. This biometric set of data is stored on the optical card in block 620. In block 624, a biometric set of data is obtained which is representative of at least one fingerprint of the optical card owner. This biometric fingerprint data is stored on the optical card in block 628. Furthermore, rather than just obtaining one fingerprint, all fingerprints of the optical card owner can be obtained and stored on the optical card. This is possible because the optical card has sufficient storage area to store a great deal of digital biometric data e.g., more than 4 MB. In addition, other data, other than biometric data could be stored as well. Thus, for example, a set of data defining a hologram could be stored for display on a computer screen. This could be used to help verify the authenticity of an optical card. In block 632, evidence of immunization of the optical card owner for a contagious disease is reviewed. In block 636, a verification is made, in view of the evidence, that the optical card owner has indeed been immunized for the contagious disease. In block 640, immunization data is stored in the storage area of the immunization card. It is intended that this immunization data only be readable by the optical card reader after the optical card reader uses the previously stored biometric sets of data stored to the optical card. Thus, this embodiment of the invention relies on multiple biometrics being measured and compared to the actual biometric characteristics presented by the optical card owner for verification. Thus, the biometric sample of the optical card owner's signature is compared to an actual signature performed by the optical card owner at the time of verification. Similarly, a high resolution image of the optical card owner can be compared to the optical card owner's actual appearance when presenting the card. Furthermore, stored fingerprint data can be compared to fingerprints received on the scene when the optical card owner presents his or her card to security personnel. These biometric tests can be performed prior to retrieving the immunization data. Thus, the optical card reader can perform a sequence of retrievals and tests prior to obtaining the immunization data from the optical card. As explained earlier, the retrieval of the optical card immunization data can be contingent upon retrieving a decryption key for use in decrypting the immunization data.

Figure 7:
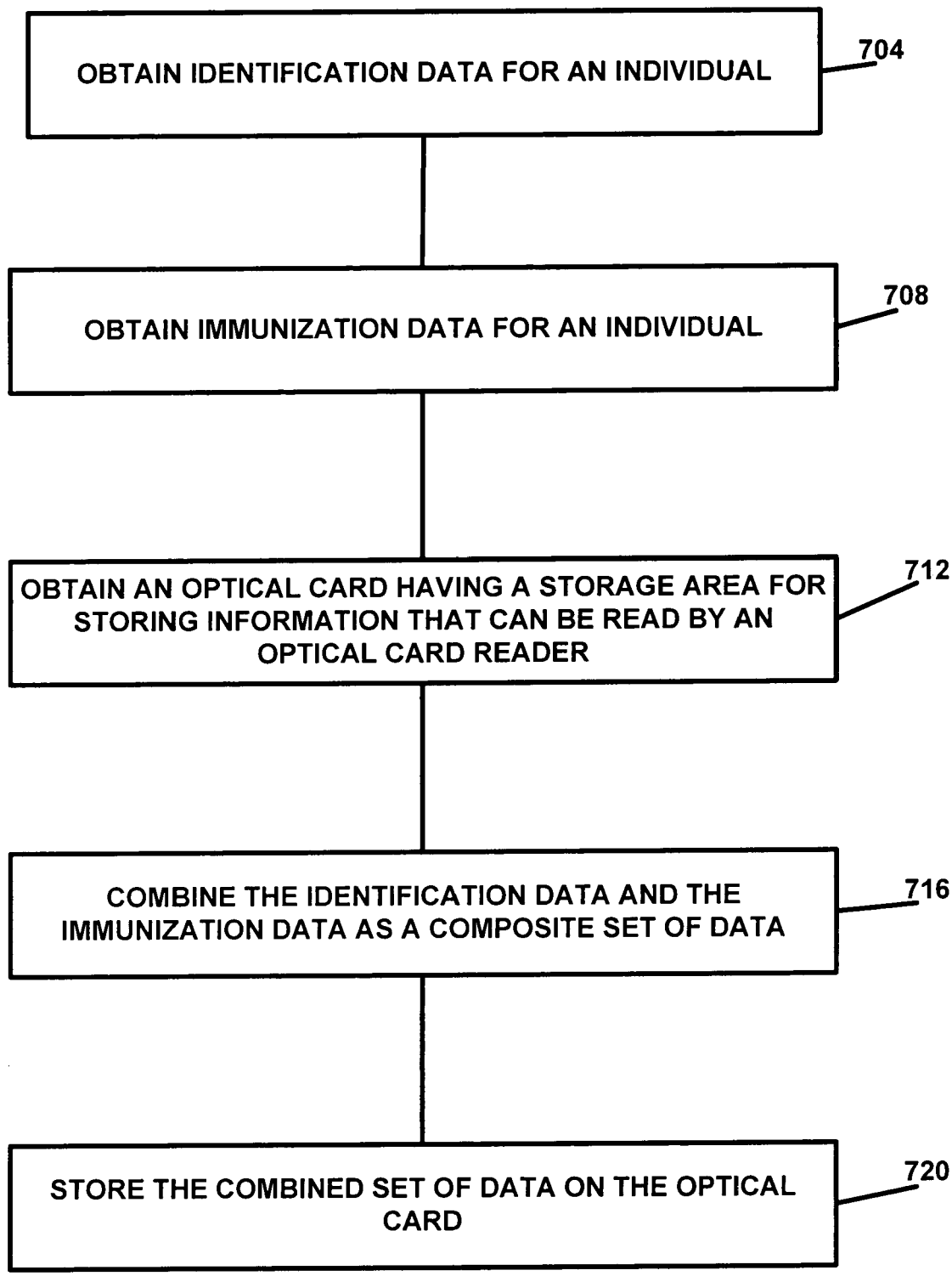
FIG. 7 is a flowchart illustrating a method of combining data in a secure fashion for an optical immunization card, according to one embodiment of the invention.
Figure 8:
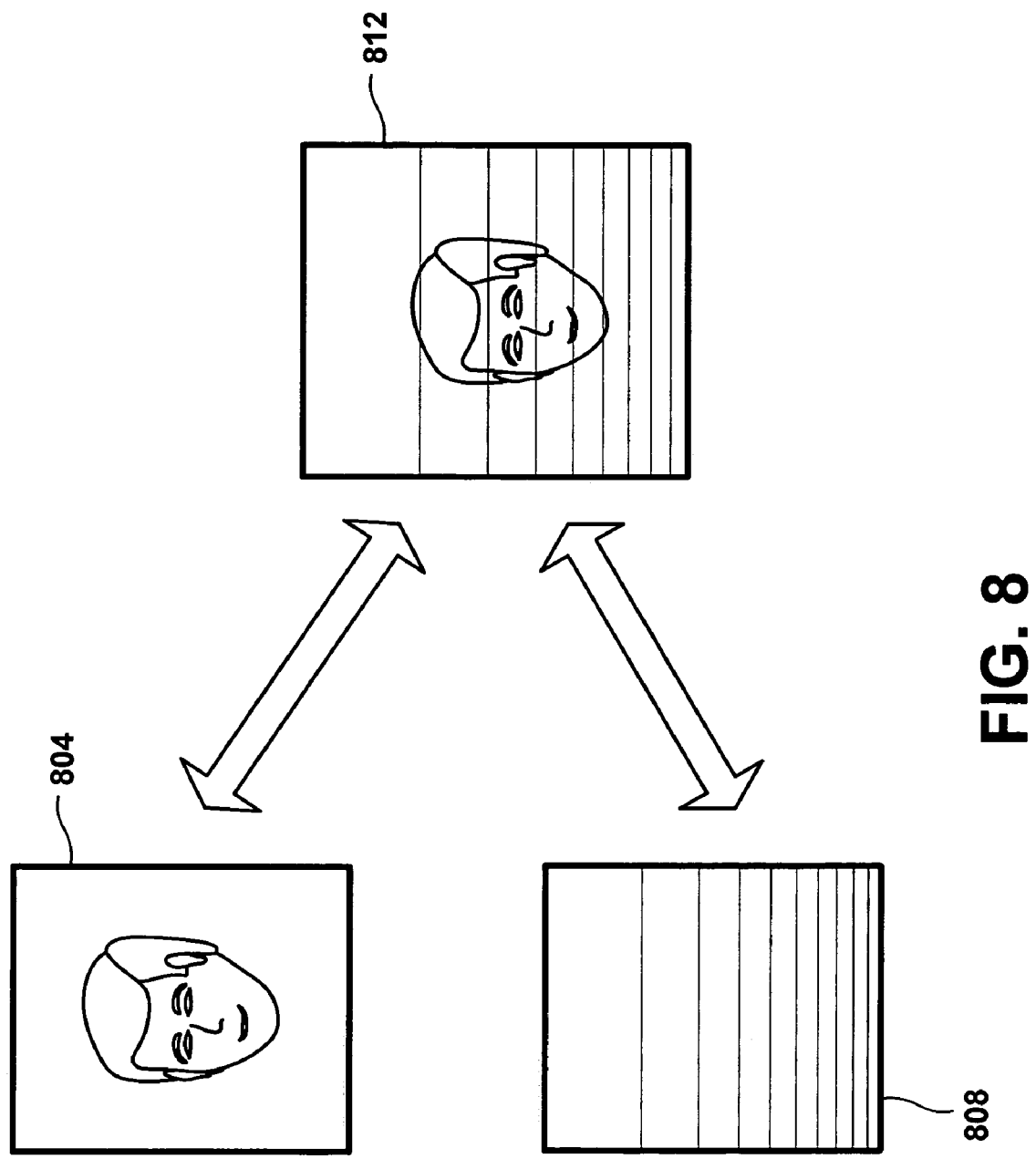
FIG. 8 is a block diagram illustrating a method of combining biometric data, according to one embodiment of the invention.

FIG. 7 illustrates an embodiment of the invention for combining biometric data with immunization data as an authentication stamp. Namely, FIG. 7 shows a flowchart 700 implementing a data combination. In block 704, identification data is obtained for an individual. Furthermore, immunization data is obtained for the same individual in block 708. An optical card having a storage area for storing information that can be read by an optical card reader is obtained in block 712. In block 716, the identification data and the immunization data are combined as a composite set of data. In block 720, the composite set of data is stored on the optical card. This is illustrated further by FIG. 8. FIG. 8 illustrates that a photo 804, for example, is combined with immunization data 808 so as to form composite data 812. Composite data 812 is shown in this example as a photograph overlaid with the immunization data. Thus, this data is probative to security personnel in that it shows the immunization data corresponds to a particular individual. Thus, it allows security personnel to review in a single data retrieval both authentication of the individual's identity and immunization status.

According to another embodiment, the identification data can be combined with immunization data to create a composite image by creating a displayable image that includes the immunization data disposed adjacent a picture of an individual. In this way, the picture of the individual would be displayed on the screen at the same time as the picture of the individual. Thus, security personnel would be able to verify that a particular individual has been immunized. The combined set of data for the picture of the individual and the immunization data can be intermixed so as to thwart attempts at modifying data on an optical card.

Figure 9:
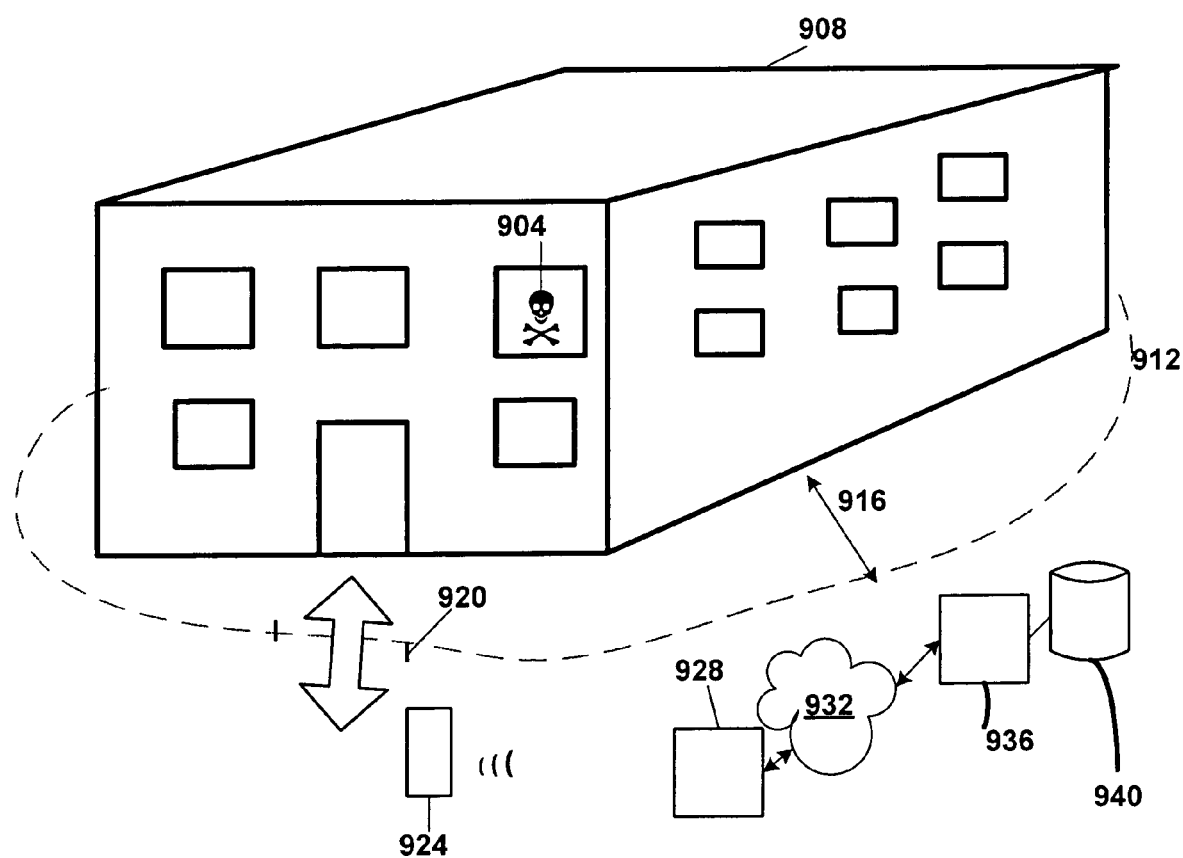
FIG. 9 is a perspective view of a biohazard site cordoned off with a perimeter for securing the biohazard site, according to one embodiment of the invention.

Referring now to FIG. 9, an implementation for an optical immunization card is shown. FIG. 9 envisions a situation where a biohazard contamination has occurred. This may be the result of an accident in a hospital or research lab. Alternatively, it may be the result of a terrorist incident in which the biohazard is introduced to a community. FIG. 9 illustrates a building 908 where a contagious element such as biohazard 904 has been introduced. This biohazard is suspected of causing contagion to spread among the people in the building. A perimeter 912 is shown surrounding the building at a suitable distance 916 where the limits of the contagion are suspected not to have yet spread. An exit or entry 920 is shown along the perimeter. Furthermore, an optical card reader 924 is shown located at the egress point. This optical card reader is indicated to be configured with a transmitter that is capable of transmitting to computer 928. Computer 928 is coupled with network 932 and computer 936. Similarly, computer 936 is coupled to database 940. Thus, FIG. 9 illustrates a system for implementing security in a biohazard location.

Figure 10A:
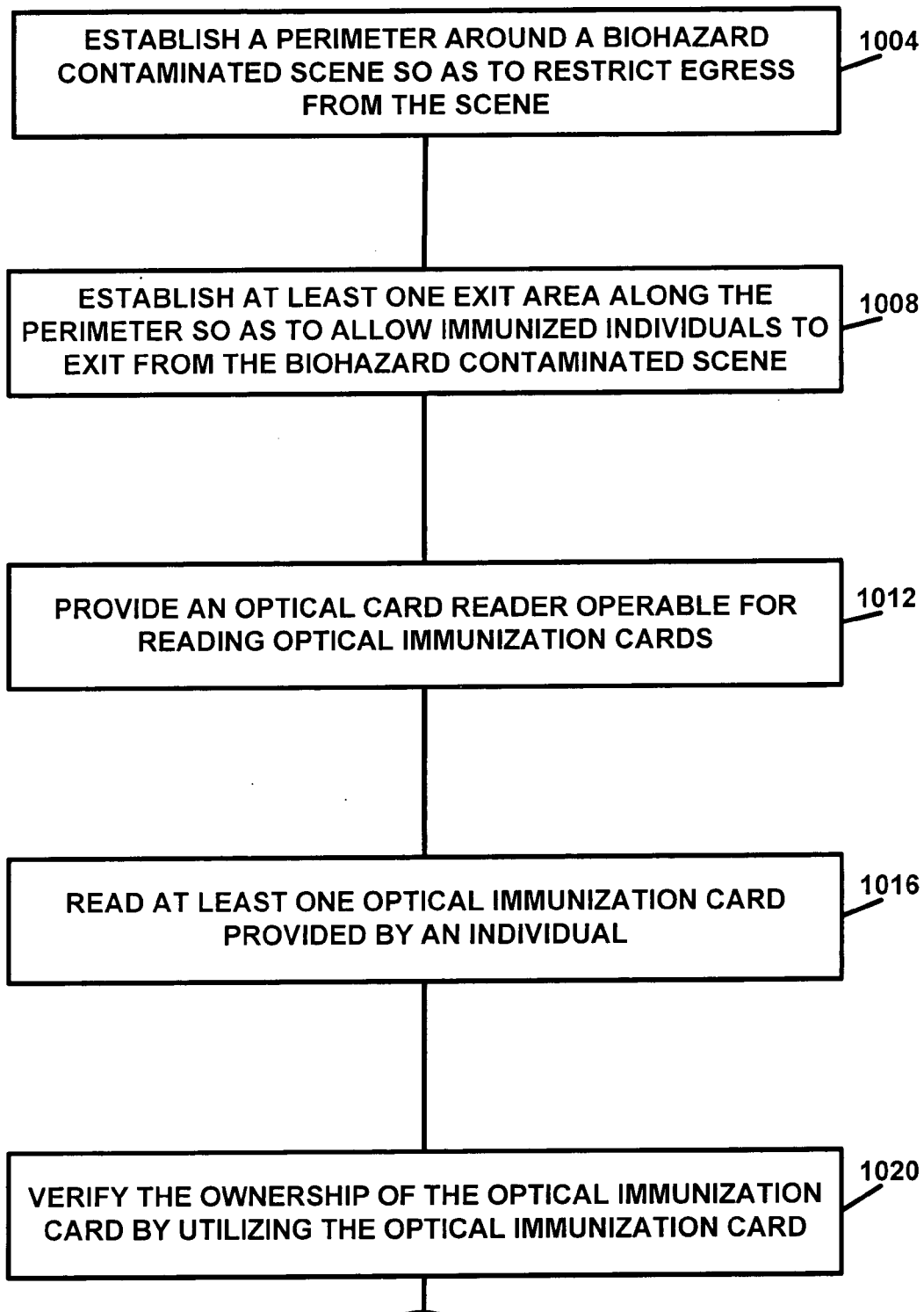

FIGS. 10A and 10B illustrate a flowchart 1000 for implementing a method for enforcing security at a biohazard contaminated scene. Namely, flowchart 1000 shows that a perimeter is established around a biohazard-contaminated scene so as to restrict egress from the scene in block 1004. In block 1008, at least one exit area is established along the perimeter so as to allow immunized individuals to exit from the biohazard-contaminated scene. In block 1012, an optical card reader is provided that is operable for reading optical immunization cards. In block 1016, at least one optical immunization card is read that is provided by an individual. In block 1020, the ownership of the optical immunization card is verified by utilizing the optical immunization card. In block 1024, the immunization data stored on the optical immunization card is checked so as to determine whether the individual is actually immunized to the biohazard. In block 1028, the optical card owner is allowed to pass through the perimeter. Thus, flowchart 1000 illustrates a method that can be implemented to establish security by requiring a person who desires to pass through the perimeter to prove their immunization to the biohazard. The person desiring to pass through the perimeter may be a person trying to exit a hospital or lab or a resident trying to exit a terrorist scene. For purposes of securing the site, especially in this day and age of highly contagious diseases, it will be preferred to ensure that the person exiting the contagious site is not at risk for infecting others outside the perimeter. Similarly, it is preferable to only allow people into a contagious area if they will not be at risk of being harmed by the contagion within the perimeter. Therefore, the present embodiment of the invention facilitates the control of entry to the biohazard site, as well.

According to one embodiment of the invention, an optical immunization card could be issued to government personnel who are in the line of work of needing to enter hazardous sites. Thus, these government personnel could be given the proper routine of immunizations so that they would be available to enter and work in biohazardous areas. Thus, according to one embodiment of the invention, this optical immunization card could be issued by storing government credentials for ingress and egress to contagious areas for which an immunization applies.

Optical immunization cards should prove valuable to society in view of their ability to help administer either an accident scene or a terrorist attack. They will not only facilitate the exit of people unaffected by the contagion due to previous immunization, but also will help facilitate the entry of health workers to the area who desire to administer to those within the biohazard area. The optical immunization card will allow quick and efficient control of the perimeter to ensure greater public health to all involved.

While various embodiments of the invention have been described as methods or apparatus for implementing the invention, it should be understood that the invention can be implemented through code coupled to a computer, e.g., code resident on a computer or accessible by the computer. For example, software and databases could be utilized to implement many of the methods discussed above. Thus, in addition to embodiments where the invention is accomplished by hardware, it is also noted that these embodiments can be accomplished through the use of an article of manufacture comprised of a computer usable medium having a computer readable program code embodied therein, which causes the enablement of the functions disclosed in this description. Therefore, it is desired that embodiments of the invention also be considered protected by this patent in their program code means as well.

It is also envisioned that embodiments of the invention could be accomplished as computer signals embodied in a carrier wave, as well as signals (e.g., electrical and optical) propagated through a transmission medium. Thus, the various information discussed above could be formatted in a structure, such as a data structure, and transmitted as an electrical signal through a transmission medium or stored on a computer readable medium.

It is also noted that many of the structures, materials, and acts recited herein can be recited as means for performing a function or steps for performing a function. Therefore, it should be understood that such language is entitled to cover all such structures, materials, or acts disclosed within this specification and their equivalents, including the matter incorporated by reference.

It is thought that the apparatuses and methods of the embodiments of the present invention and its attendant advantages will be understood from this specification. While the above is a complete description of specific embodiments of the invention, the above description should not be taken as limiting the scope of the invention as defined by the claims.

What is claimed is:

1. A method of recording immunization data, said method comprising:
   obtaining identification data for an individual;
   obtaining immunization data for said individual;
   obtaining an optical card comprising a storage area for storing information accessible via an optical card reader;
   combining said identification data and said immunization data as a composite set of data;
   storing said composite set of data on said optical card;
   wherein said identification data comprises a picture of said individual and wherein said combining said identification data and said immunization data comprises:
   making an overlaid composite image of said immunization data and said picture of said individual so that said immunization data and said picture of said individual at least partially overlap when viewed.

2. An optical immunization card comprising:
   an optical card comprising a storage area for storing information accessible via an optical card reader;
   a first area of said optical card storing set of data representative to an optical card reader of a first biometric of a picture of said optical card owner;
   a second area of said optical card storing a first biometric set of data representative to said optical card reader of a first biometric of said optical card owner wherein said first biometric comprises a fingerprint of said optical card owner;
   a third area of said optical card storing a second biometric set of data representative to said optical card reader of a second biometric of said optical card owner wherein said second biometric is a signature of said optical card owner;
   a fourth area of said optical card storing an immunization record for said optical card owner, wherein said immunization record is readable by said optical card reader after said optical card reader utilizes said first biometric set of data and said second biometric set of data and said picture of said optical card owner;
   wherein said second area of said optical card stores biometric data for each finger of said optical card owner.

3. A method of programming an optical immunization card for use at a biohazardous site, said method comprising:

obtaining an optical card for an optical card owner, said optical card comprising a storage area for storing information accessible via an optical card reader;

obtaining a picture of said optical card owner;

storing said picture of said optical card owner on said optical card;

obtaining a first biometric set of data representative of a signature of said optical card owner;

storing said first biometric set of data in said storage area of said optical card;

obtaining a second biometric set of data representative of a fingerprint of said optical card owner;

storing said second biometric set of data in said storage area of said optical card;

reviewing evidence of immunization of said optical card owner for a contagious disease;

verifying that said optical card owner has been immunized for said contagious disease;

storing immunization data in said storage area of said card, wherein said immunization data is readable by said optical card reader after said optical card reader utilizes said biometric set of data and said second biometric set of data;

wherein said second biometric set of data comprises biometric data for each fingerprint of said optical card owner.

* * * * *